(12) United States Patent
Liddy et al.

(10) Patent No.: US 9,314,325 B2
(45) Date of Patent: Apr. 19, 2016

(54) ANTI-ASPIRATION PROSTHESIS

(71) Applicant: Cook Medical Technologies LLC, Bloomington, IN (US)

(72) Inventors: Alison Liddy, Salthill (IE); Michael Ryan, Dooradoyle (IE); Gerard Treacy, Castletroy (IE); Ger Houlihan, Kilmallock (IE); Shay Joseph Lavelle, Annacotty (IE); John Neilan, Gort (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/790,640

(22) Filed: Mar. 8, 2013

(65) Prior Publication Data
US 2013/0289740 A1    Oct. 31, 2013

Related U.S. Application Data

(60) Provisional application No. 61/639,217, filed on Apr. 27, 2012.

(51) Int. Cl.
*A61F 2/04* (2013.01)
*A61F 2/24* (2006.01)

(52) U.S. Cl.
CPC ............ *A61F 2/04* (2013.01); *A61F 2/2412* (2013.01); *A61F 2/2415* (2013.01); *A61F 2002/044* (2013.01); *Y10T 29/49426* (2015.01)

(58) Field of Classification Search
CPC . A61F 2/04; A61F 2250/0018; A61F 2/2403; A61F 2/2418; A61F 2002/044; A61F 2002/045; A61F 2002/046; A61F 2/15; A61F 2/2412
USPC .......... 623/23.68, 23.64, 23.65, 23.66, 23.67, 623/23.69, 23.7, 1.24, 2.14, 2.15, 2.16, 623/2.17, 2.18, 2.36, 2.37, 2.38
See application file for complete search history.

(56) References Cited

U.S. PATENT DOCUMENTS 4,434,810 A    3/1984    Atkinson
4,846,836 A    7/1989    Reich
(Continued)

FOREIGN PATENT DOCUMENTS

EP    1 430 853 B1    6/2004
EP    1 704 834 B1    9/2006
(Continued)

OTHER PUBLICATIONS

International Search Report mailed Jan. 9, 2014 for International Application No. PCT/US2013/037965.
(Continued)

*Primary Examiner* — David Isabella
*Assistant Examiner* — Rokhaya Diop
(74) *Attorney, Agent, or Firm* — Brinks Gilson & Lione

(57) ABSTRACT

A prosthesis and a method of manufacturing the prosthesis for controlling flow through a bodily lumen are provided. The prosthesis includes a body having a proximal portion, a distal portion and a lumen extending therethrough. The prosthesis also includes a valve operably connected to the body. The valve has a proximal portion, a distal portion and a lumen extending through the valve, where the valve lumen is connected to the body lumen. The valve is configured to be closed in the absence of an antegrade pressure and a retrograde pressure, the retrograde pressure being greater than the antegrade pressure. The valve includes a material portion operably connected to the valve, the material portion providing increased stiffness to the valve relative to the valve alone, wherein the material portion is configured to facilitate self-reversion of the valve to the closed configuration.

12 Claims, 15 Drawing Sheets

(56) References Cited

U.S. PATENT DOCUMENTS

| | | | |
|---|---|---|---|
| 5,314,473 A | 5/1994 | Godin | |
| 5,392,775 A | 2/1995 | Adkins, Jr. et al. | |
| 5,554,181 A * | 9/1996 | Das | 623/1.12 |
| 5,861,036 A | 1/1999 | Godin | |
| 6,203,321 B1 | 3/2001 | Helmer et al. | |
| 6,264,700 B1 * | 7/2001 | Kilcoyne et al. | 623/23.68 |
| 6,302,917 B1 | 10/2001 | Dua et al. | |
| 6,544,291 B2 | 4/2003 | Taylor | |
| 6,746,489 B2 | 6/2004 | Dua | |
| 6,790,237 B2 | 9/2004 | Stinson | |
| 7,118,600 B2 | 10/2006 | Dua et al. | |
| 7,182,788 B2 | 2/2007 | Jung et al. | |
| 7,354,455 B2 | 4/2008 | Stinson | |
| 7,993,410 B2 | 8/2011 | Shin et al. | |
| 8,029,557 B2 | 10/2011 | Sobrino-Serrano et al. | |
| 8,221,505 B2 | 7/2012 | Skerven | |
| 2003/0040808 A1 | 2/2003 | Stack et al. | |
| 2005/0137681 A1 * | 6/2005 | Shoemaker et al. | 623/1.23 |
| 2007/0213813 A1 | 9/2007 | Von Segesser et al. | |
| 2008/0086214 A1 | 4/2008 | Hardin et al. | |
| 2008/0300678 A1 * | 12/2008 | Eidenschink et al. | 623/2.18 |
| 2009/0138071 A1 | 5/2009 | Cheng et al. | |
| 2009/0171447 A1 | 7/2009 | Von Segesser et al. | |
| 2010/0036504 A1 | 2/2010 | Sobrino-Serrano et al. | |
| 2010/0114327 A1 | 5/2010 | Sobrino-Serrano | |
| 2010/0121461 A1 | 5/2010 | Sobrino-Serrano et al. | |
| 2010/0121462 A1 | 5/2010 | Sobrino-Serrano et al. | |
| 2010/0137998 A1 * | 6/2010 | Sobrino-Serrano et al. | 623/23.68 |
| 2011/0160836 A1 | 6/2011 | Behan | |
| 2011/0190905 A1 | 8/2011 | Behan | |
| 2012/0059486 A1 | 3/2012 | Sobrino-Serrano et al. | |
| 2012/0158026 A1 | 6/2012 | Behan | |
| 2012/0197386 A1 | 8/2012 | Von Segesser et al. | |

FOREIGN PATENT DOCUMENTS

| | | |
|---|---|---|
| EP | 1 952 785 B1 | 8/2008 |
| EP | 2 248 486 A2 | 11/2010 |
| EP | 2 316 381 A2 | 5/2011 |
| EP | 2 368 527 A1 | 9/2011 |
| EP | 2 387 973 A1 | 11/2011 |
| WO | WO 03/030782 A1 | 4/2003 |
| WO | WO 2006/004679 A1 | 1/2006 |
| WO | WO 2008/028569 A1 | 3/2008 |
| WO | WO 2011/073970 A1 | 6/2011 |

OTHER PUBLICATIONS

Written Opinion mailed Jan. 9, 2014 for International Application No. PCT/US2013/037965.

* cited by examiner

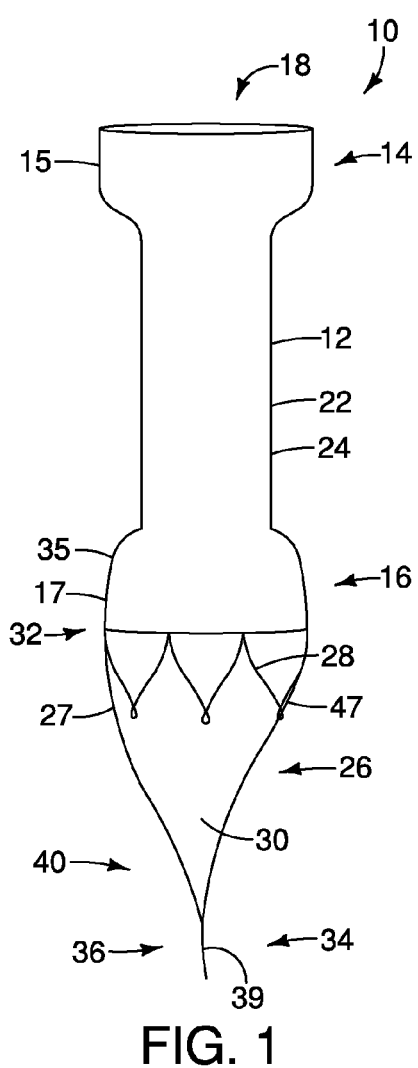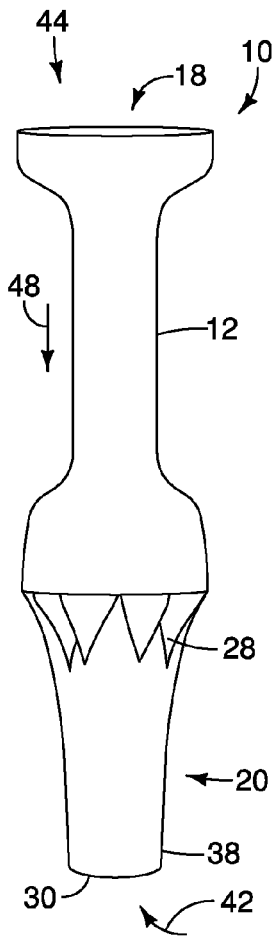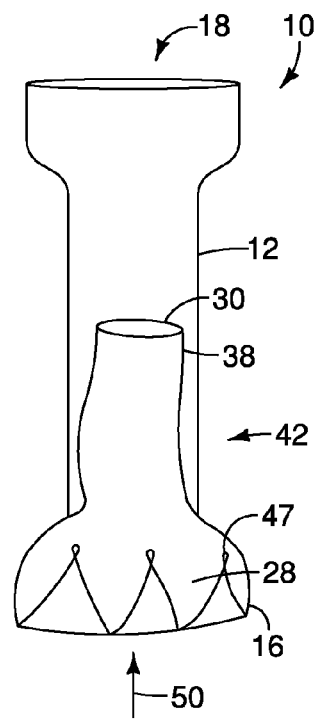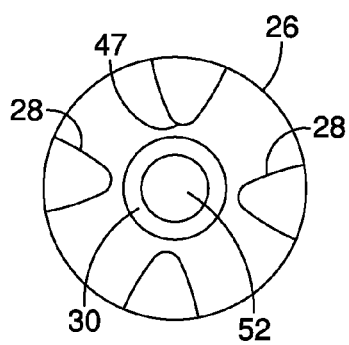
FIG. 1
FIG. 2
FIG. 3
FIG. 4

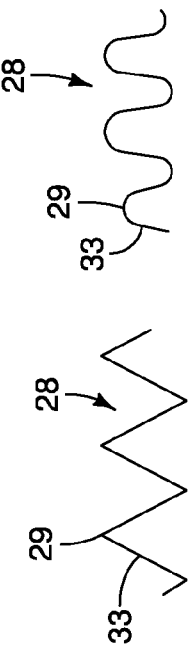
FIG. 9A
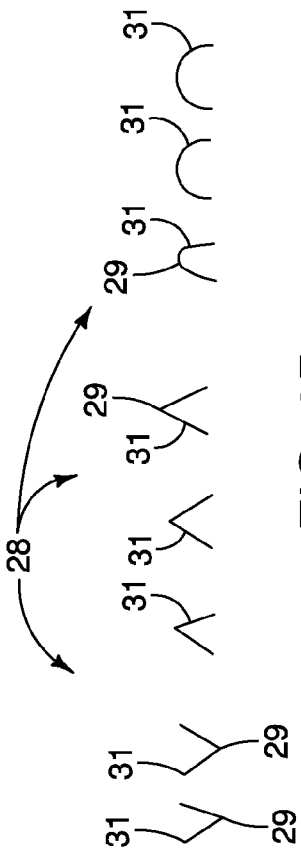
FIG. 9B
FIG. 9C
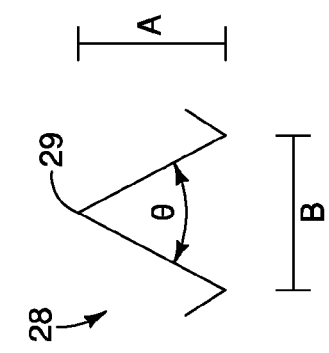
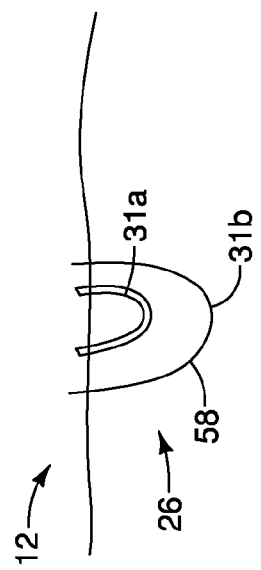
FIG. 10

ANTI-ASPIRATION PROSTHESIS

RELATED APPLICATIONS

This application claims the benefit of U.S. Provisional Application No. 61/639,217, filed Apr. 27, 2012, which is incorporated by reference herein in its entirety.

FIELD OF THE INVENTION

The present invention relates to medical devices and in particular to a valve for regulating fluid flow therethrough.

BACKGROUND OF THE INVENTION

The lower esophageal sphincter (LES) in healthy individuals allows food to pass into the stomach, but prevents gastric fluids from moving into the esophagus except when the patient vomits. Aspiration is a clinical risk for patients having a malfunctioning LES or for patients having stents placed across the gastroesophageal junction (GEJ) so that an opening is created at the bottom of the esophagus that can lead to acid reflux and aspiration. Aspiration occurs when the stomach contents travel from the stomach into the lungs. Aspiration in the lungs can lead to pneumonia or death. Risk of aspiration in patients having a compromised LES increases when the patient is in a prone position.

Anti-reflux esophageal prostheses or stents have been developed to treat tumors or strictures in the vicinity of the LES. Anti-reflux esophageal prosthesis or stent is typically placed in the lower esophagus and through the LES to maintain the patency thereof due to the presence of a cancerous tumor commonly found in the vicinity thereof or to treat benign tumor conditions, such as blockage or strictures.

A problem with an esophageal prosthesis or stent is that fluid from the stomach flows into the mouth of the patient when in a prone position, increasing the risk of aspiration. In an attempt to solve the problem, a number of esophageal prostheses or stents utilize a one-way valve such as a duck-bill or reed-type valve in which only food or fluid from the esophagus flows into the stomach in only an antegrade or forward direction. However, these one-way anti-reflux prostheses or stents present another problem. When the patient wants to belch or vomit, the patient is prevented from doing so, because the one-way valve prevents backward flow in the retrograde direction. Such condition is not only painful to the patient, but can also lead to more complicated medical conditions.

What is needed is a prosthesis that is normally closed to prevent gastric fluids from entering the esophagus, allows food to pass into the stomach and also allows for vomiting and belching when necessary and returns to the closed position.

BRIEF SUMMARY

Accordingly, it is an object of the present invention to provide a device and a method of manufacturing the device having features that resolve or improve on the above-described drawbacks.

A prosthesis and a method of manufacturing the prosthesis for controlling flow through a bodily lumen are provided. The prosthesis includes a body having a proximal portion, a distal portion and a lumen extending therethrough. The prosthesis also includes a valve operably connected to the body. The valve has a proximal portion, a distal portion and a lumen extending through the valve, where the valve lumen is connected to the body lumen. The valve is configured to be closed in the absence of an antegrade pressure and a retrograde pressure, the retrograde pressure being greater than the antegrade pressure. The valve includes a material portion operably connected to the valve, the material portion providing increased stiffness to the valve relative to the valve alone, wherein the material portion is configured to facilitate self-reversion of the valve to the closed configuration. In some embodiments, the material portion includes at least one material that may be made from a different material than a valve material. In some embodiments, the material portion may be the same material as that of the valve but be formed into such a way that enables the valve to self-revert. This can be achieved by using a change in the material portion relative to the remainder of the valve such as a thickened portion of valve material which is incorporated into one section of the valve. This section of material is designed to not possess the same flexibility as the valve material. Therefore under a certain pressure the valve inverts however due to the rigid section it quickly reverts back to the preformed shape.

BRIEF DESCRIPTION OF THE DRAWINGS

FIG. 1 is a side view of a prosthesis in accordance with an embodiment of the present invention in a closed configuration;

FIG. 2 is a side view of the prosthesis shown in FIG. 1 in an open configuration in response to flow in an antegrade direction;

FIG. 3 is a side view of the prosthesis shown in FIG. 1 in an inverted configuration in response to flow in a retrograde direction;

FIG. 4 is an end view of a prosthesis in accordance with an embodiment of the present invention;

FIGS. 9A-9C illustrate alternative embodiments of the material portion of the prosthesis;

FIG. 10 is a partial side view of an embodiment of the material portion;

DETAILED DESCRIPTION

Figure 5:
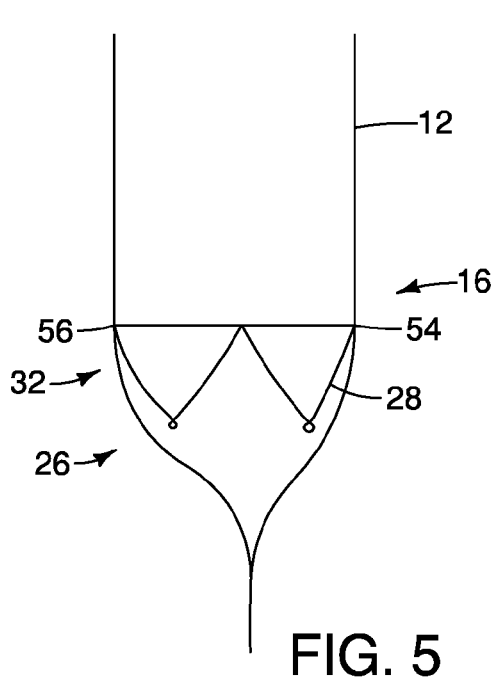
FIG. 5 is a partial side view of an embodiment of a prosthesis in accordance with the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the prosthesis to a patient. Hence the term "distal" means the portion of the prosthesis that is farthest from the physician and the term "proximal" means the portion of the prosthesis that is nearest to the physician.

The present invention relates to medical devices, and in particular to prosthetic devices for implantation in a body lumen such as the esophagus, the vasculature, the urinary tract and the biliary tree. As used herein, the term "implantable" refers to an ability of a medical device to be positioned at a location within a body, such as within a body lumen, either temporarily, semi-permanently, or permanently. Permanent fixation of the device in a particular position is not required. Furthermore, the terms "implantation" and "implanted" refer to the positioning of a medical device at a location within a body, such as within a body lumen.

FIG. 1 illustrates a prosthesis 10 in accordance with an embodiment of the present invention. The prosthesis 10 includes a body 12 having proximal portion 14, a distal portion 16 and a lumen 18 extending therethrough. In some embodiments, the body 12 may be an expandable stent such as a self-expandable stent or a balloon expandable stent. Non-limiting examples of expandable stents include the Z-STENT and the EVOLUTION® stent (Cook Medical, Inc. Bloomington, Ind.). In some embodiments, the body 12 may be a non-expandable tubular stent. The proximal portion 14 of the body 12 may include an end portion 15 having an expanded outer diameter and the distal portion 16 may include an end portion 17 having an expanded outer diameter. In some embodiments, the body 12 may be a substantially straight tubular shape. The body 12 may include a coating or a sleeve 22 extending through or around the body 12 that is liquid impermeable so that liquid and nutrients flowing from the proximal portion 14 to the distal portion 16 or stomach contents from the distal portion 16 to the proximal portion 14 do not pass through a wall 24 of the body 12. As shown in FIG. 1, the prosthesis 10 includes a valve 26. In some embodiments, the valve 26 may be contiguous with the coating or sleeve 22 and in some embodiments the valve 26 may be separately provided. The valve 26 includes a lumen 30 operably connected to the lumen 18 of the body 12. The valve 26 is configured to control fluid flow through the prosthesis 10. The valve 26 may be provided as a formed valve where the valve is formed to be closed to form a protective barrier reducing the risk of stomach contents entering the valve 26 in the retrograde direction, especially when a patient is in a prone position. The valve 26 includes a material portion 28 that is incorporated into, onto or throughout the valve 26 as will be described in more detail below. The valve may be any shape. Exemplary shapes are shown and described below.

Referring to the embodiment shown in FIG. 1, the valve 26 is operably connected to the body 12 and extends distally from the distal portion 16 of the body 12. In some embodiments, a proximal portion 32 of the valve 26 is connected to the body 12. A distal portion 34 of the valve 26 is configured to extend into the patient's stomach. The valve 26 is shown in a closed configuration 36 in FIG. 1 where a distal end portion 38 of the valve 28 is closed upon itself so that stomach contents cannot flow from in the retrograde direction from the stomach to the esophagus or lungs of the patient. A first pressure 40 is normally present in stomach and the valve 26 is configured to normally be closed in the presence of the first pressure 40 or in the absence of any pressure, for example when the patient is in a prone position.

FIG. 2 illustrates the valve 26 of the prosthesis 10 in an open configuration 42 in response to a second pressure 44 that occurs when liquid and nutrients flow from the mouth and pass to the stomach. The second pressure 44 is greater than the first pressure 40. The nutrients travel in an antegrade direction 48 through the lumen 18 of the body 12 and into the lumen 30 of the valve 26 to the stomach. The distal end portion 38 of the valve 26 opens in response to the second pressure 44 to allow flow from the mouth to the stomach. In the absence of the second pressure 44, the valve 26 is configured to return to the closed configuration 40 shown in FIG. 1.

FIG. 3 illustrates the valve 26 in the open configuration 42 in response to a third pressure 50 that is greater than the first and second pressures 40, 42. For example, when the patient needs to belch or vomit, the valve 26 opens in response to the third pressure 50. The third pressure 50 pushes at least a portion of the valve 26 proximally to evert the valve 26 so that the distal end portion 38 of the valve 26 extends proximally. The valve 26 opens so that the third pressure 50 built up in the stomach may be relieved through the mouth. In the absence of the second or the third pressure 42, 50, the valve 26 returns to the closed configuration 40 shown in FIG. 1. After the third pressure 50 is removed, in some embodiments, the valve 26 may be re-inverted so that the distal end portion 38 extends distally. In some embodiments, the valve 26 may be re-inverted by the patient swallowing water or by the material portion 28 returning to its original position.

As shown in FIGS. 1-3, the valve 26 includes the material portion 28 that may provide one or more of the advantages described below. The material portion 28 may be provided to introduce a stiffness or rigidity into the valve 26 that is greater than the stiffness of the valve 26 alone. In some embodiments, the stiffness can be introduced without needing to increase the thickness of a wall of the valve 26. In other embodiments, the thickness of the wall of the valve 26 may also be increased. The increased stiffness or rigidity added by the material portion 28 may also facilitate better loading, delivery and recapturing of the prosthesis 10 so that the valve 26 does not become blocked in the delivery system. The material portion 28 may also help the valve 26 to self-revert and return to closed configuration by providing a spring-like effect so that the distal end portion 38 extends distally after the third pressure 50 has been relieved. By way of non-limiting example, the material portion 28 may be formed of a resilient material that springs into shape, such as a shape memory material or a polymer that may be provided as a wire or a sheet. In some embodiments, the nitinol may be heat set. Other materials are also possible. By way of non-limiting example, material may include metal alloys such as stainless steel, tantalum or its alloys, tungsten, platinum, gold, copper, palladium, rhodium, or a superelastic alloys, such as nitinol or polymers that can be provided with sufficient shore hardness, such as PEBAX, Peek, polyimide, liquid crystal polymers (LCP) such as VECTRAN, polyethylene, polyethylene terephthalate and Nylon. In some embodiments, the material may be nitinol and in some embodiments the nitinol may be heat set. In some embodiments, the material portion 28 is made from a different material than the valve 26. In some embodiments, the material portion 28 may be made of the same material as the valve 26. The material portion 28 may be provided at a proximal portion, a distal portion, through the entirety of the valve 26 or at any portion of the valve 26. In some embodiments, the material portion 28 may be provided on a side of the valve 26.

In some embodiments, the material portion may be formed from heat set nitinol or formed to allow the valve 26 to self-return. In this embodiment, the material portion 28 comprising the nitinol arm/spring may be attached to an external surface 27 of the valve 26. Once the valve 26 moves in response to the retrograde flow and the retrograde flow is stopped, the nitinol arm/spring rapidly pulls the valve 26 back to the original shape of the valve. In some embodiments, the material portion 28 comprising the nitinol arm/spring may be attached to a surface 35 of the body 12. In other embodiments, the material portion may be connected to an interior surface of the valve 26 or embedded within the valve 26. In some embodiments, the material portion is connected to the valve and is not connected to the body 12. In some embodiments, the material portion 28 may be formed from an elastomeric material and connected to the valve 26 and/or the body 12 similarly to the nitinol arm/spring described above. In some embodiments, the material portion 28 may be connected to an interior of the body 12.

As shown in the end view in FIG. 4, the material portion 28 may bend inward towards a center 52 of the valve 26 in the presence of the third pressure 50 to facilitate the proximal extension of the distal end portion 38 of the valve 26 and the opening of the lumen 30. In some embodiments, a distal end 47 of the material portion 28 may extend across a portion of the distal portion 16 of the body 12 as shown in FIG. 4. In some embodiments, the distal end 47 of the material portion 28 may extend into the lumen 18 of the body 12 as shown in FIG. 3. The material portion 28 may then spring back to its original position where the distal end 47 of the material portion 28 extends distally when the third pressure 50 is relieved which also helps return the valve 26 to the closed configuration 40.

When the material portion 28 is provided on or in the proximal portion 32 of the valve 26, the material portion 28 may be operably connected to the distal portion 16 of the body 12. As shown in FIG. 5, the material portion 28 may be connected to a distal end 54 of the body 12 so that a proximal end 56 of the material portion 28 extends distally from the distal end 54 of the body 12. The entire material portion 28 is free to move inward in response to the third pressure 50 to facilitate the proximal extension of the distal end portion 38 of the valve 26 and the opening of the lumen 30. In some embodiments, the material portion 28 may be directly connected to the distal end 54 and in some embodiments, the material portion 28 may be connected to the valve 26 and the valve 26 is connected directly to the body 12. The material portion 28 may be configured to extend inward toward the center 52 as shown in FIG. 4.

Figure 6:
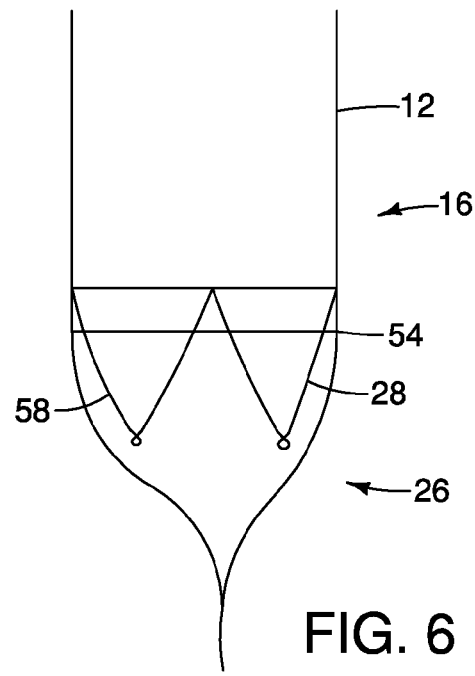
FIG. 6 is a partial side view of an alternative embodiment of a prosthesis in accordance with the present invention.

As shown in FIG. 6, in some embodiments the material portion 28 may be operably connected to the body 12 at a position proximal to the distal end 54 of the body 12 so that the material portion 28 partially overlaps the body 12. The material portion 28 may be operably connected to the body 12 within the lumen 18 or external to the body 12. A distal portion 58 of the material portion 28 may move inward in response to the third pressure 50 and the distal end portion 38 of the valve 26 may extend proximally and the lumen 30 may be opened. The distal portion 58 of the material portion 28 may then spring back to its original position when the third pressure 50 is relieved which also helps return the valve 26 to the closed configuration 40.

Figure 7:
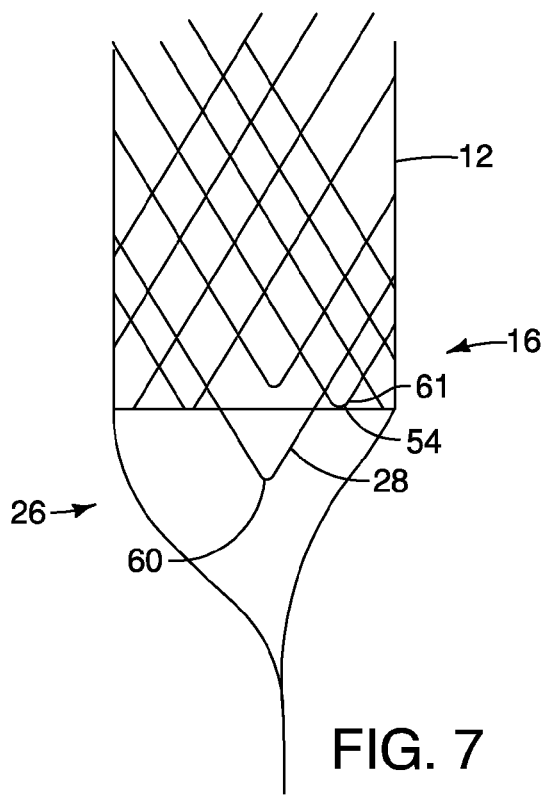
FIG. 7 is a partial side view of an alternative embodiment of a prosthesis in accordance with the present invention.
Figure 8A:
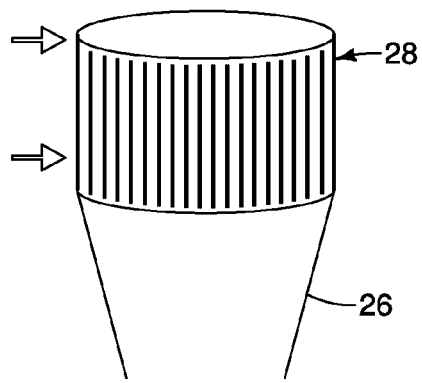
FIGS. 8A-8E illustrate alternative embodiments of the material portion of the prosthesis of the present invention.
Figure 8B:
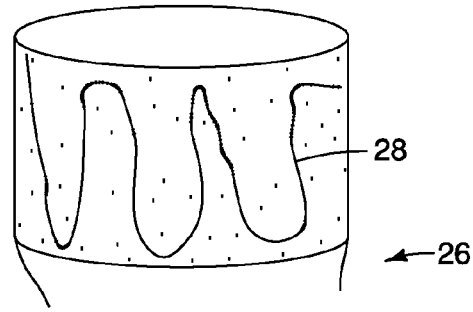
Figure 8C:
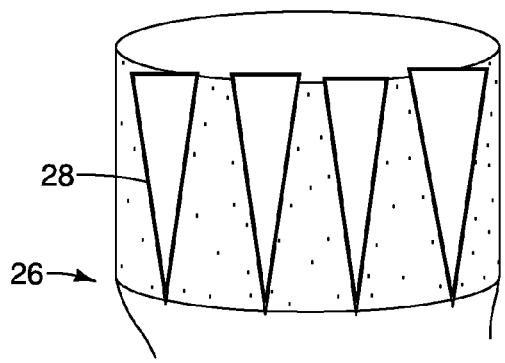
Figure 8D:
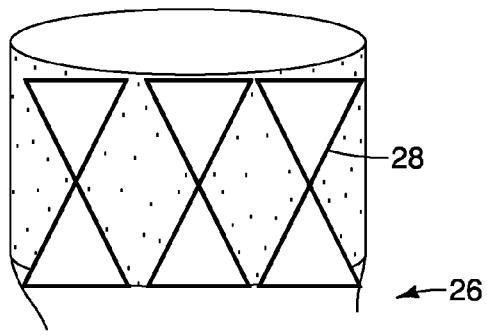
Figure 8E:
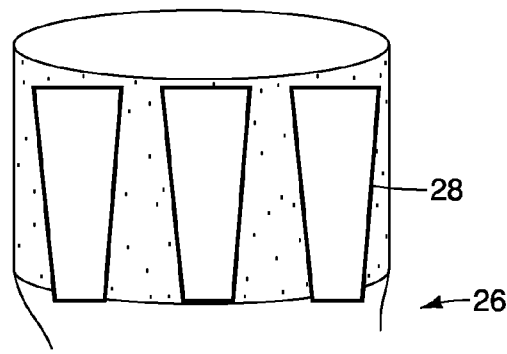

FIG. 7 illustrates an alternative embodiment of the material portion 28. As shown, the material portion 28 may be formed as an extension of the body 12. For example, when the body 12 is formed as a woven mesh, one or more ends 60 of the body 12 may be distally extended relative to other ends 61 so that a subset of ends 60 of the body 12 form the material portion 28. The material portion 28 shown in FIG. 7 may bend and spring back to position similar to the embodiments described above.

The material portion 28 may be provided in many different shapes or patterns. In addition to the pattern shown in FIG. 1, exemplary patterns for the material portion 28 are shown in FIGS. 8A-8E. By way of non-limiting example, the material portion 28 may include the following shapes or patterns: strips, mesh, diamond, u-shaped, circular, zig-zag, crisscross, v-shaped spring and the like. Additional shapes and patterns are also possible for the material portion 28. Any of the patterns may be operably connected to the body 12 in accordance with any of the embodiments described above.

The spacing and the positioning of the material portion 28 may also be varied to change the flexibility of the material portion 28. For example, as shown in FIG. 9A, the flexibility of the material portion 28 may be varied by increasing or decreasing the length A or by increasing or decreasing the length B that also changes the angle θ at a peak 29 of the material portion 28. FIG. 9B illustrates that the material portion 28 may be formed from a plurality of independent members 31 that are separate from each and independently operably connected to the valve 26. FIG. 9C illustrates an alternative embodiment showing that the material portion 28 may be formed from a continuous member 33 having a plurality of peaks 29 and operably connected to the valve 26. The shape of the members 31 and 33 may vary, for example having peaks 29 that are arched or curved. Other shapes for the peaks may also be used.

In some embodiments, the material portion 28 may be formed by a pair of independent members 31a, 31b at the same position on or in the valve 26 as shown in FIG. 10. A plurality of pairs 31a, 31b may be positioned in or on the valve 26 in some embodiments. A first member 31a may be positioned within a second member 31b and extending along the same plane. The first and second members 31a, 31b may have the same flexibility or different flexibilities. In some embodiments, the first member 31a may have a thicker diameter and thus be more rigid than the second member 31b. In some embodiments, the first and second members 31a, 31b may have the same diameter. The flexibility of the material portion 28 is stiffer closer to the body 12 where four wires of the first and second members 31a, 31b extend along the same plane. The material portion 28 is more flexible at the distal portion 58 where two wires extend along the same plane.

Figure 11B:
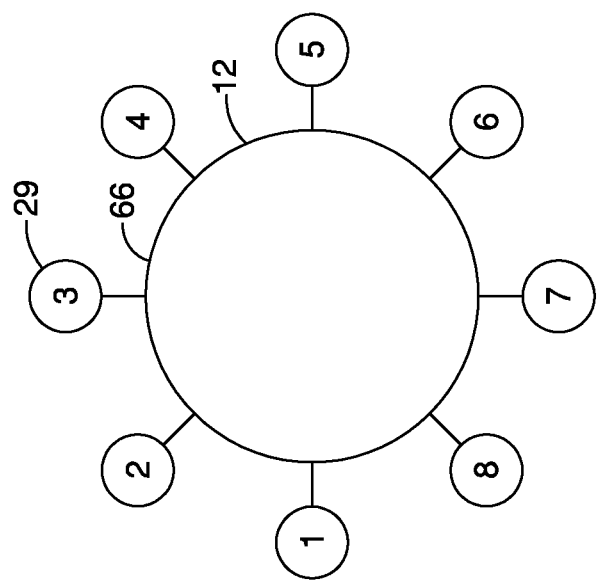
FIGS. 11A and 11B illustrate embodiments for positioning the material portion around a perimeter of the body of the prosthesis in accordance with the present invention.
Figure 11A:
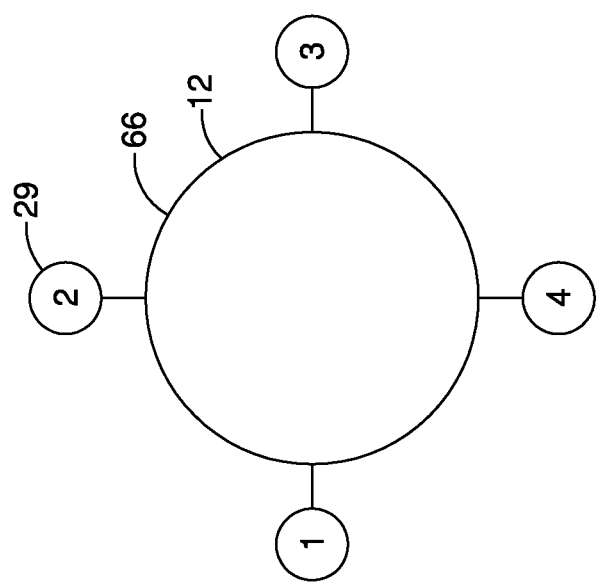

When the material portion 28 includes a plurality of peaks 29 on a continuous member 33, the number of peaks 29 may be varied as shown in FIGS. 11A and 11B. The position of the peaks 29 are indicated by numbers shown on the end view of the body 12. As shown in FIG. 11A, four peaks 29 may be provided for the material member 28. The peaks 29 may be equidistantly spaced apart around a perimeter 66 of the body 12 or in some embodiments, the spacing between the peaks 29 may be unequal. In some embodiments, the angle θ of each of the peaks 29 may increase as the valve 26 expands, for example as food passes through the valve 26. The angle θ of each of the peaks 29 may decrease as the valve 26 collapses. Some of the peaks 29 may be configured to resist bending in response to the third pressure 50 and some of the peaks 29 may be configured to facilitate bending in response to the third pressure 50. These peaks 29 may be alternated to help the valve 26 return to the closed configuration 40 when the third pressure is relieved.

Figure 12:
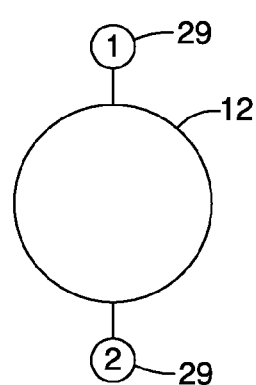
FIG. 12 illustrates an embodiment of the position of the material portion around a perimeter of the body.
Figure 13:
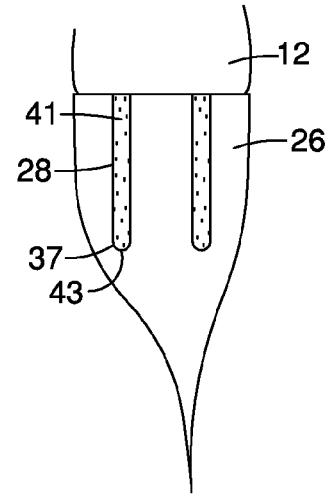
FIG. 13 is a partial side view of an alternative embodiment of a material portion.

In some embodiments, the material portion 28 may be formed from two independent peaks 29 spaced equidistance apart from each other on the valve 26 as shown in FIG. 12. The peaks 29 may be connected to the body 12 or to the valve 26 similar to the embodiments described above. The peak 29 may be positioned so that the peak 29 of the material portion 28 extends distally away from the body 12 or extends proximally toward the body 12. In some embodiments, the material portion 28 may be formed from one or more straight wires 37 that are operably connected to the valve 26 as shown in FIG. 13.

Figure 14:
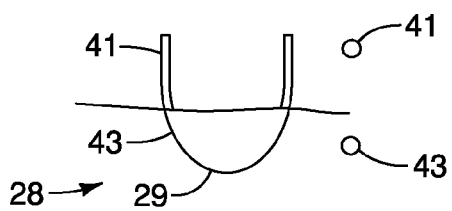
FIG. 14 is a partial side view of an alternative embodiment of a material portion.

One or more of the peaks 29 of the material portion may be treated so that a proximal portion 41 of the peak 29 may be more rigid than a distal portion 43 of the peak 29 as shown in FIG. 14. The difference between the proximal portion 41 and the distal portion 43 may be used regardless of the shape of the material portion 28. For example, the wire 37 shown in FIG. 13 may have different flexibilities in the proximal and distal portions 41, 43. By way of non-limiting example, the difference in flexibility of the material portion 28 may be provided by electropolishing, chemically etching or grinding the distal portion 43 of the material portion 28. FIG. 14 illustrates the difference in the diameter of the proximal portion 41 and the distal portion 43 after electropolishing or chemical etching. The more flexible distal portion 43 may be helpful in preventing the material portion 28 from damaging the valve 26.

Figure 15:
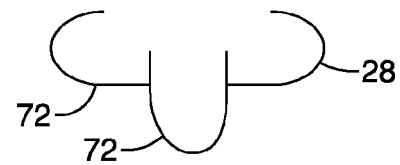
FIG. 15 illustrates an embodiment of the material portion.
Figure 16:
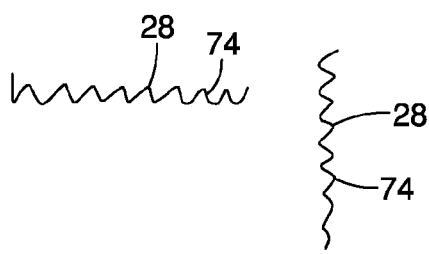
FIG. 16 illustrates an alternative embodiment of the material portion.
Figure 17:
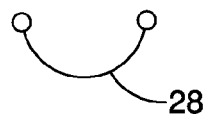
FIG. 17 illustrates an alternative embodiment of the material portion.

In some embodiments, the material portion 28 may be provided within the valve 26 or connected to the body 12. As shown in FIG. 15, the material portion 28 may include one or more loop portions 72 to facilitate the return of the valve 26 to the closed configuration after the retrograde flow has ceased. FIG. 16, illustrates an embodiment of the material portion 28 that may include one or more springs or arms 74 that are provided with the valve 26 to facilitate the return of the valve 26 to the closed configuration after the retrograde flow has ceased. The springs 74 may be coiled and may be provided in any direction, for example parallel to the axis of the body 12 or perpendicular to the axis of the body 12 or at an angle to the axis of the body 12 or in combinations of directions. FIG. 17 illustrates an alternative embodiment of the material portion 28 where the material portion 28 is curved to facilitate the movement of the valve 26 toward the body 12/into the body 12 in response to retrograde flow and to facilitate the return of the valve 26 to the closed configuration.

Figure 18:
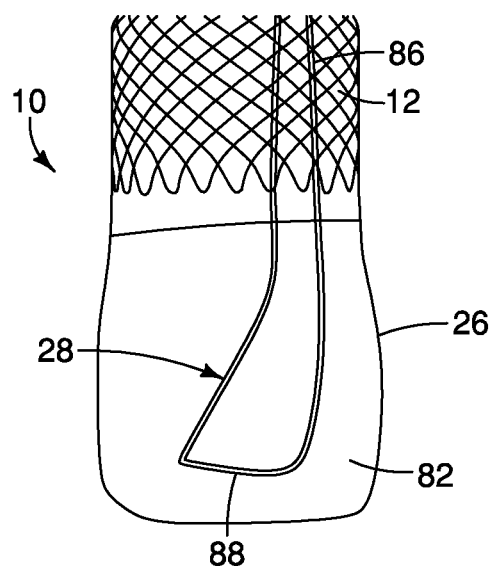
FIG. 18 illustrates an embodiment of the material portion positioned on/in the valve.
Figure 19:
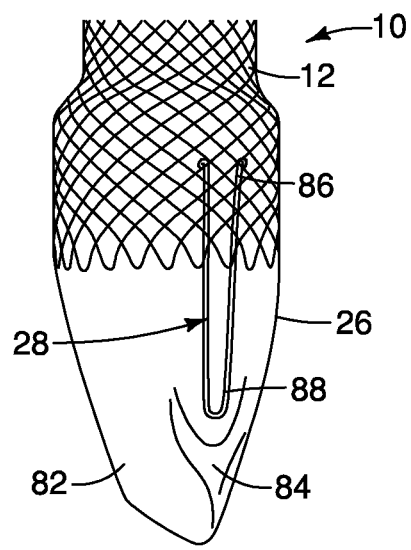
FIG. 19 illustrates an embodiment of the material portion positioned on/in the valve.
Figure 20:
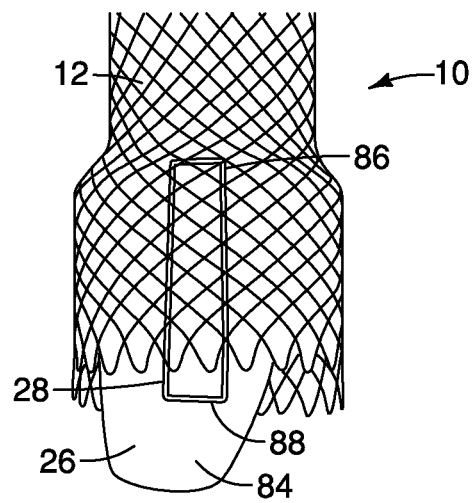
FIG. 20 illustrates an embodiment of the material portion positioned on/in the valve.

In some embodiments, the prosthesis 10 may be provided with a material portion 28 that is a single arm that is incorporated onto or within the valve 26 as shown in FIGS. 18-20. The single arm material portion 28 may be provided on or in any portion of the valve 26. By way of non-limiting example, the single arm material portion 28 is shown positioned on a flattened face 82 of the valve 26 in FIG. 18. In some embodiments, the face may be an angled face where the arm is formed at the same angle that the valve is formed so that the material portion 28 fits into the valve on the angled face. A proximal portion 86 of the material portion 28 is shown connected to the body 12 of the prosthesis 10 in FIGS. 18 and 19. FIG. 20 illustrates the proximal portion 86 of the material portion 28 embedded within the valve 28 and unconnected to the body 12. FIGS. 19 and 20 illustrate the single arm material portion 28 positioned on a side 84 of the valve 26 away from the flattened face 82. In some embodiments, the single arm material portion 28 may be generally u-shaped with a distal portion 88 of the material 28 forming the "u." The distal portion 88 of the material 28 may be wider than the proximal portion 86. In some embodiments, the distal portion 88 may be the same width or narrower than the proximal portion 86. As discussed above, the material portion 28 may be positioned on any portion of the valve. In some embodiments, the material portion 28 may be a single arm and in other embodiments, the material portion 28 may be a plurality of arms as described above.

Figure 21A:
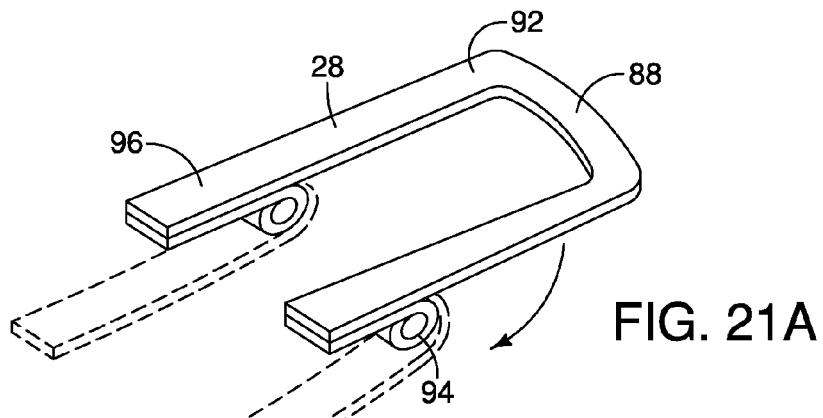
FIGS. 21A and 21B illustrate an embodiment of the material portion that may be formed from a sheet of material.
Figure 21B:
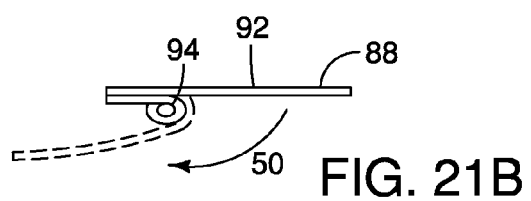

Additional configurations for the material portion 28 are shown in FIGS. 21-42. By way of non-limiting example, the material portion may be made from a sheet of material such as nitinol. Exemplary sheet configurations are shown in FIGS. 21A-25B where the material portion may be formed from one or more layers of material. FIG. 21A illustrates the material portion 28 having a first portion 92 that is u-shaped and a second portion 94 that is operably connected to one or more ends 96 of the "u" so that the distal end 88 of the "u" can fold over on the second portion 94 in response to the pressure 50. FIG. 21B shows a side view of the embodiment in FIG. 21A.

Figure 22:
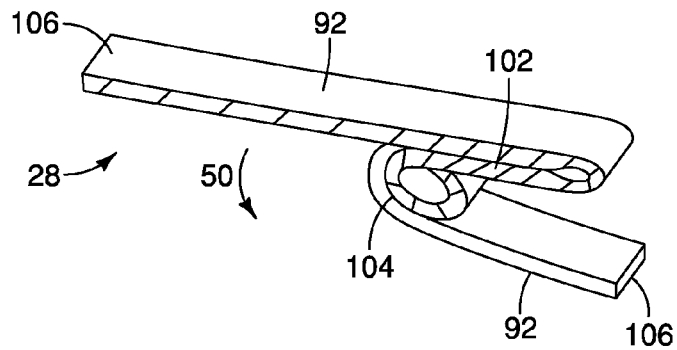
FIG. 22 illustrates an embodiment of the material portion that may be formed from a sheet of material.
Figure 23:
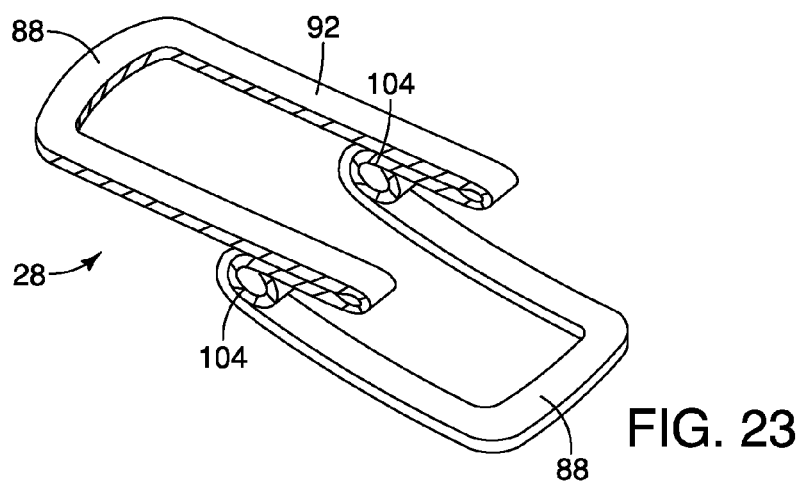
FIG. 23 illustrates an embodiment of the material portion that may be formed from a sheet of material.

FIG. 22 illustrates the material portion 28 formed from a single layer of material that is folded onto itself. The first portion 92 may include a portion 102 that is folded onto itself and that may also include a coil 104. An end 106 of the first portion 92 may bend over the coil 104 in response to the pressure 50 and then return the original configuration after the pressure 50 is removed. FIG. 23 illustrates an embodiment similar to FIG. 22 and includes the u-shaped first portion 92 and a pair of coils 104. The distal portion 88 is configured to fold over the coils 104 in response to the pressure 50 and then return to the original configuration after the pressure is removed.

Figure 24A:
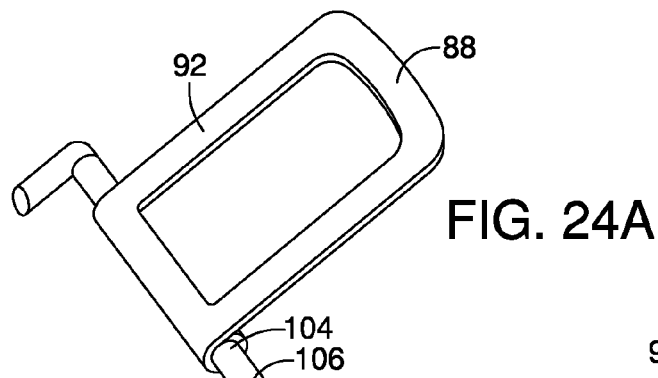
FIGS. 24A and 24B illustrate an embodiment of the material portion that may be formed from a sheet of material.
Figure 24B:
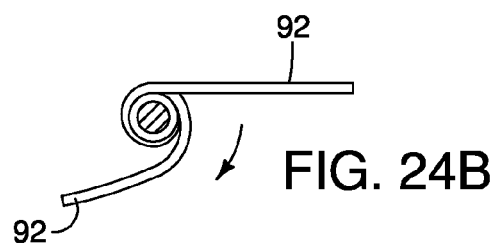

FIGS. 24A and 24B illustrate an embodiment of the material portion 28 having a pivotable arm. The material portion 28 may be made for one or more layers of material, such as a sheet of nitinol. The material portion includes the first portion 92 that may have a u-shaped configuration although other shapes are also possible. The first portion 92 includes one or more coils 104 and the first portion 92 is configured to pivot on a fixed shaft 106. The fixed shaft 106 may be connected to the body 12 of the prosthesis 10. The distal end portion 88 is configured to pivot toward the proximal portion 14 of the body 12 (not shown) in response to the pressure 50. In some embodiments, the distal portion 88 may also be flexible and bend toward the proximal portion 86. The material portion 28 is configured to return to the original configuration in the absence of the pressure 50.

Figure 25A:
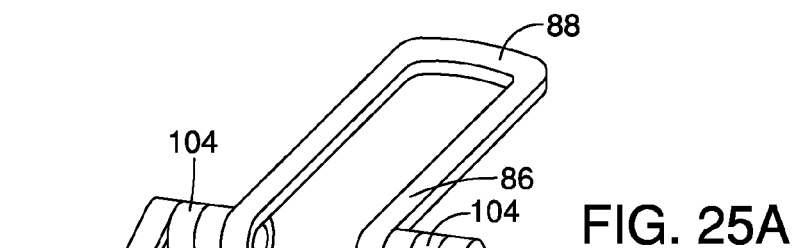
FIGS. 25A and 25B illustrate an embodiment of the material portion that may be formed from a sheet of material.
Figure 25B:
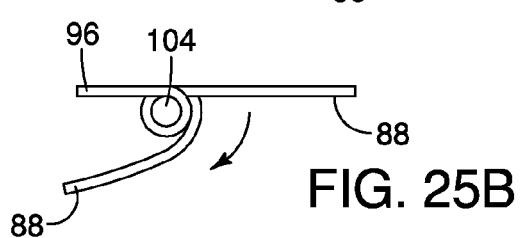
Figure 26:
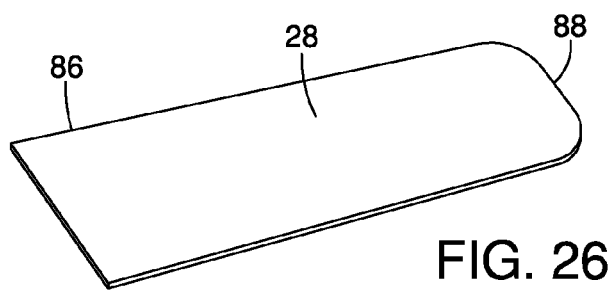
FIG. 26 illustrates an embodiment of the material portion that may be formed from a sheet of material.

FIGS. 25A and 25B illustrate an embodiment of the material portion 28 having a plurality of coils 104 so that the distal portion 88 of the first portion 92 can fold toward the proximal portion 86 in response to the pressure 50. The material portion 28 may be made for one or more layers of material, such as a sheet of nitinol. The material portion 28 includes the first portion 92 that may have a u-shaped configuration although other shapes are also possible. The first portion 92 includes a plurality of coils 104 and two fixed ends 96. The fixed ends 96 may be connected to the body 12. The distal end portion 88 is configured to move toward the proximal portion 14 of the body 12 (not shown) in response to the pressure 50. The plurality of coils 104 facilitates the movement of the distal portion 88 toward the proximal portion 86. In some embodiments, the distal portion 88 may also be flexible and bend toward the proximal portion 86. The material portion 28 is configured to return to the original configuration in the absence of the pressure 50.

Figure 27:
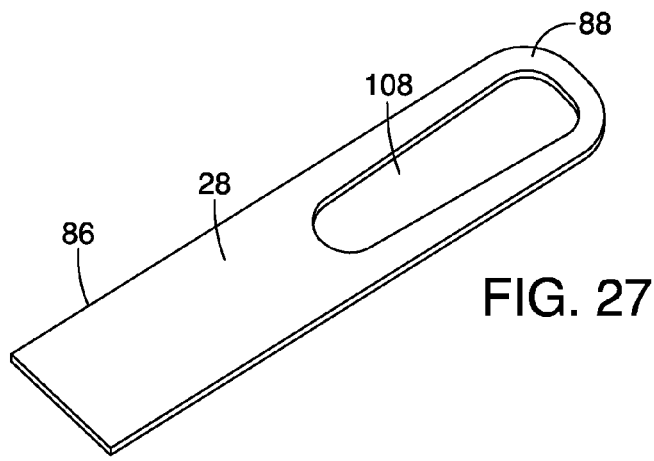
FIG. 27 illustrates an embodiment of the material portion that may be formed from a sheet of material.
Figure 28:
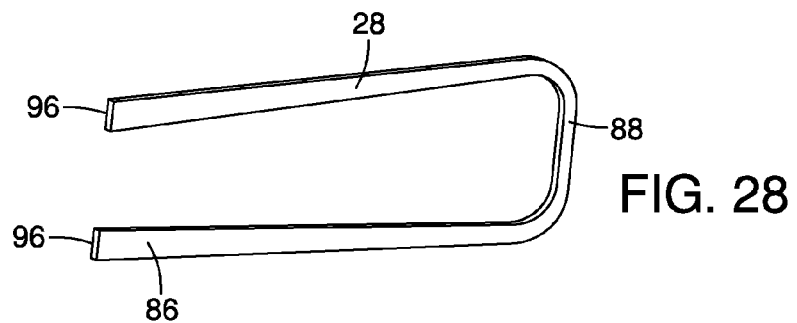
FIG. 28 illustrates an embodiment of the material portion that may be formed from a sheet of material.
Figure 29:
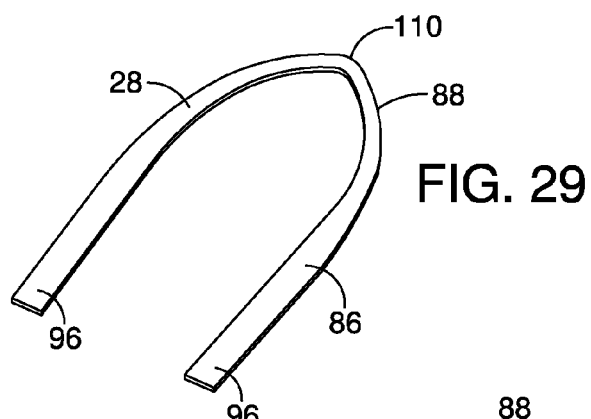
FIG. 29 illustrates an embodiment of the material portion that may be formed from a sheet of material
Figure 30:
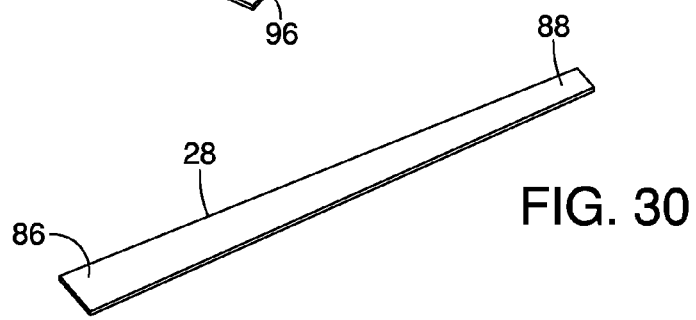
FIG. 30 illustrates an embodiment of the material portion that may be formed from a sheet of material.
Figure 31:
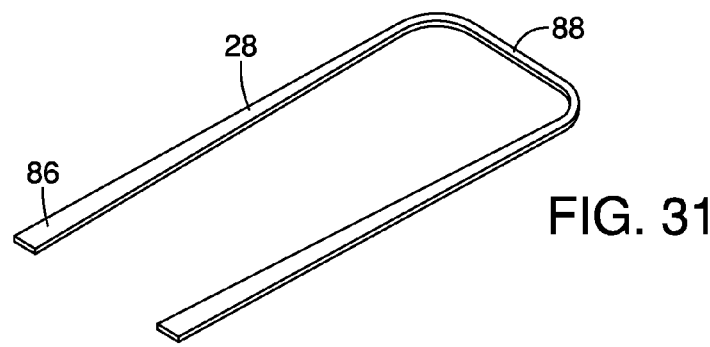
FIG. 31 illustrates an embodiment of the material portion that may be formed from a sheet of material.

FIGS. 26-31 illustrate embodiments of the material portion 28 that may be formed from a sheet of material. In some embodiments, the sheet may be a nitinol sheet or other type of shape memory material or combinations thereof. The sheet may also be a polymer or a combination of a polymer and a metal or any material have sufficient spring-like characteristics. The material portion 28 includes the proximal portion 86 and the distal portion. In some embodiments, the distal portion 88 may be formed to be thinner relative to the proximal portion 86 to increase flexibility of the distal portion 88. In other embodiments, the proximal portion 86 may be formed to be thinner relative to the distal portion 88 to increase flexibility of the proximal portion 86. In some embodiments, such as shown in FIG. 27, the distal portion 88 may include an opening 108 to increase flexibility of the distal portion 88. The embodiment shown in FIG. 27 may also include a thinner distal portion 88. As shown in FIGS. 28 and 31, the u-shape at the distal portion 88 may have a narrower arm width relative to the ends 96 and/or the proximal portion 86. In some embodiments, the "u" may be wider than the ends 96 as shown in FIG. 28 and in some embodiments the "u" may narrow or have an arch shape 110 as shown in FIG. 29. FIG. 30 illustrates an embodiment of the material portion 28 that tapers to a narrower distal portion 88 relative to the proximal portion 86. The embodiment shown in FIG. 30 may also have a thinner distal portion 88 relative to the proximal portion 86 or a thinner proximal portion 86 relative to the distal portion 88.

Figure 32:
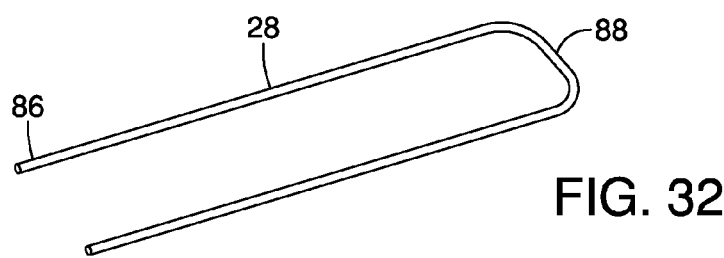
FIG. 32 illustrates an embodiment of the material portion that may be formed from a wire.

FIGS. 32-38 illustrate embodiments of the material portion 28 where the material portion 28 may be formed from a wire. The wire may be any kind of wire suitable to flex and return in response to pressure exerted on the material portion 28. In some embodiments, the wire may be made from nitinol or other shape memory material, although other materials are also possible. In some embodiments, the nitinol wire may be heat treated, etched, ground, electropolished or otherwise treated to facilitate bending in some portions of the wire. The material portion 28 may be a u-shaped wire as shown in FIG. 32. Similar to embodiments described above, the material portion made of wire may have a thinner wire at the distal portion 88 relative to the proximal portion 86 or a thinner wire at the proximal portion 86 relative to the distal portion 88.

Figure 33:
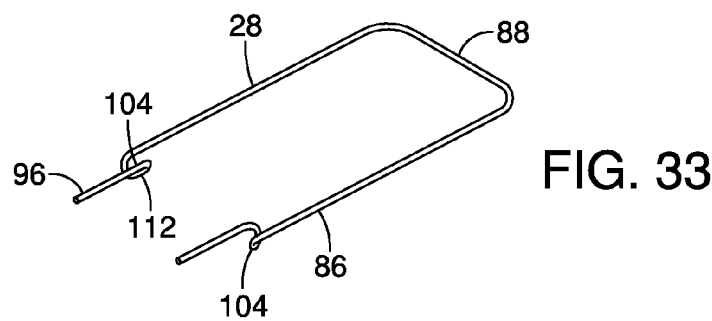
FIG. 33 illustrates an embodiment of the material portion having a coil.
Figure 34:
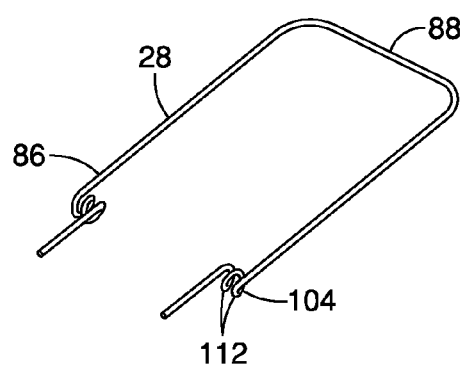
FIG. 34 illustrates an embodiment of the material portion having a coil.
Figure 35:
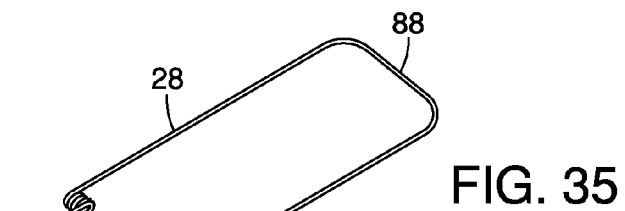
FIG. 35 illustrates an embodiment of the material portion having a coil.
Figure 36:
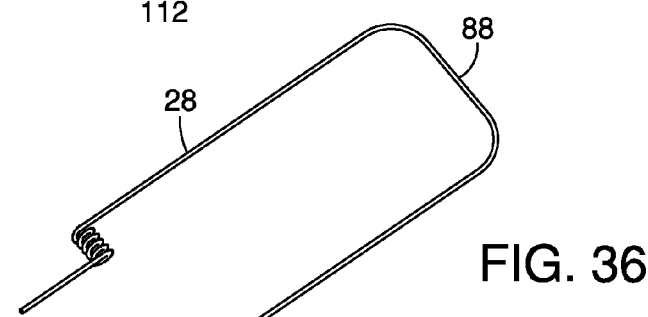
FIG. 36 illustrates an embodiment of the material portion having a coil.
Figure 37:
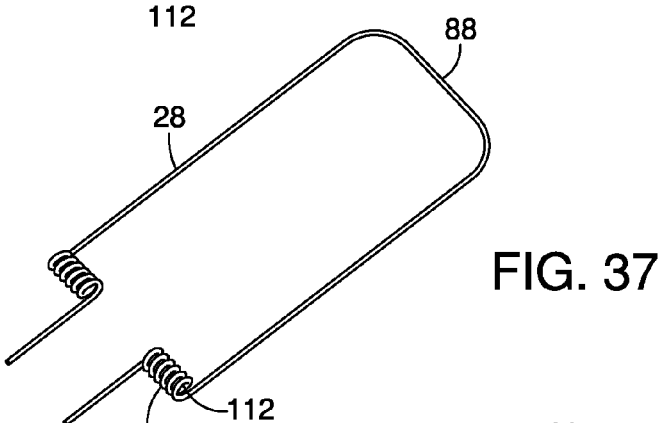
FIG. 37 illustrates an embodiment of the material portion having a coil.

In some embodiments, the material portion 28 may include one or more coils 104 as shown in FIGS. 33-38. As shown in FIG. 33, the material portion 28 includes the coil 104 having a single turn 112. The embodiment shown in FIG. 33 includes two coils 104, each coil 104 positioned distal to the ends 96 and proximal to the u-shaped distal portion 88. FIGS. 34 to 37 show embodiments having increasing numbers of turns 112 in the coils 104 and FIG. 37 illustrates the turns 112 coiled in a different direction relative to the turns 112 shown in FIGS. 34-36. In some embodiments, the material portion 28 may have a coil 104 including 1, 2, 3, 4, 5, 6 or more turns. These embodiments also illustrate different dimensions for the u-shaped distal portion 88.

Figure 38:
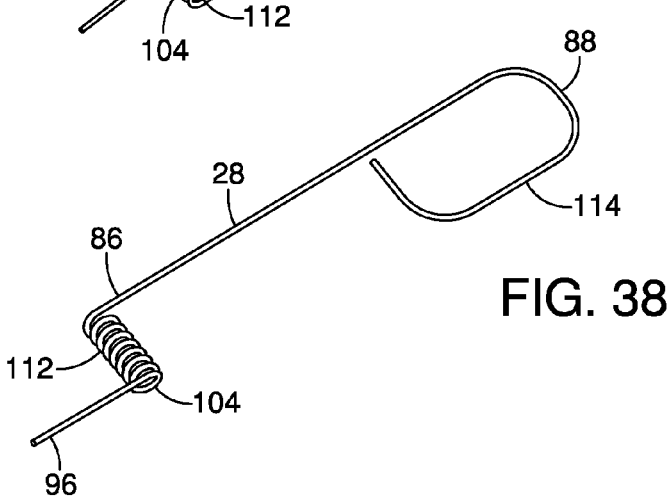
FIG. 38 illustrates an embodiment of the material portion having a coil.
Figure 42:
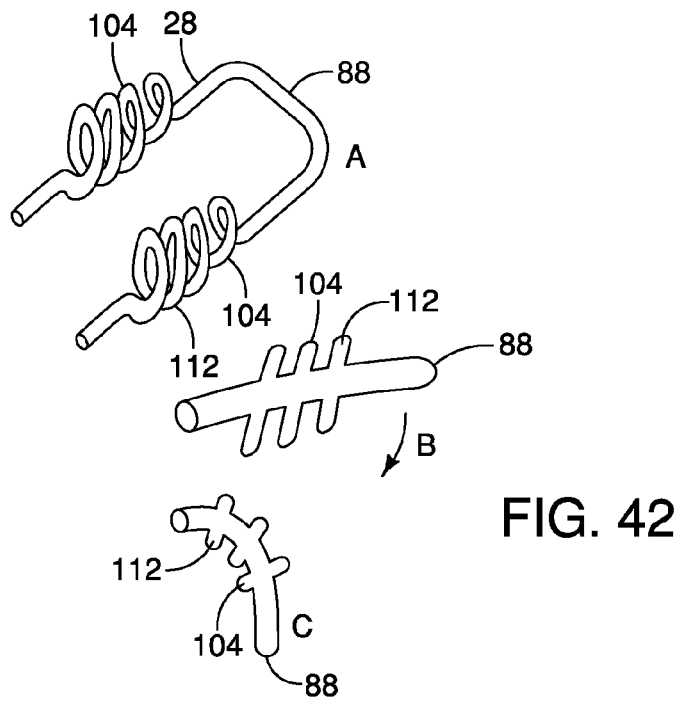
FIG. 42A-42C illustrate an embodiment of the material portion having a coil.

FIG. 38 illustrates an alternative embodiment of the material portion 28 that may be formed from a wire. The proximal portion 86 includes the coil 104 having a plurality of turns 112 that are distal to the proximal end 96. The distal portion 88 of the material portion shown in FIG. 38 includes a loop 114. In the embodiments shown in FIGS. 33-38, the coils 104 are shown extending generally parallel to the bottom of the "u" in the distal portion 88. However, the coils 104 may extend generally perpendicular to the bottom of the "u" in the distal portion B8 as shown in FIG. 42.

Figure 39:
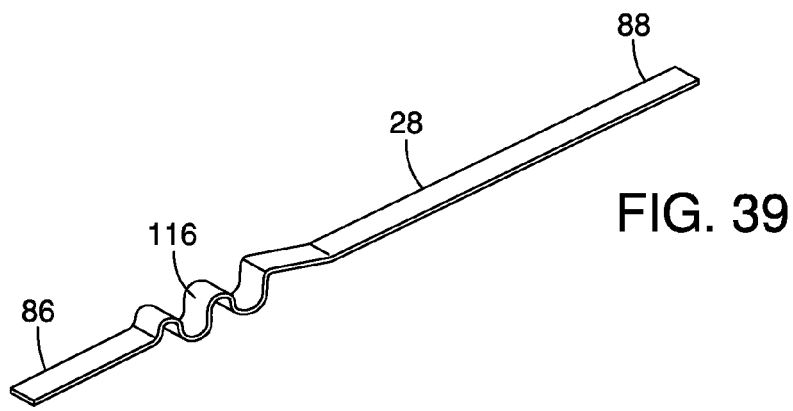
FIGS. 39 and 40 illustrate embodiments of the material portion having an undulation.
Figure 40:
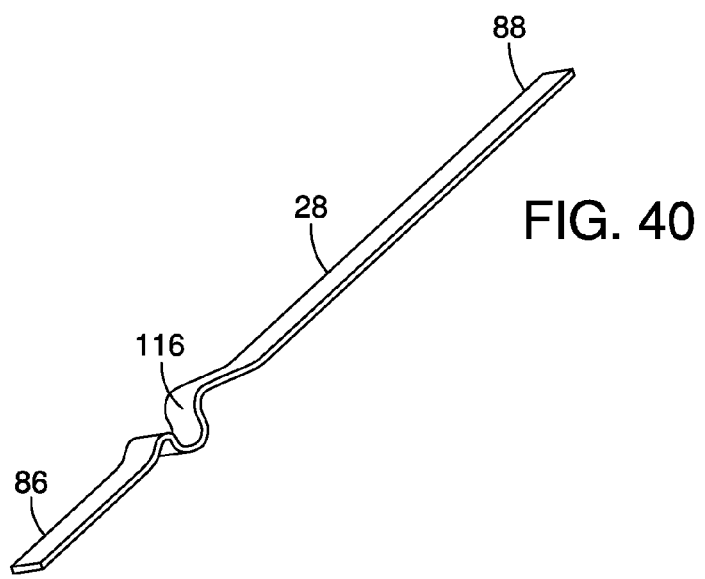
Figure 41:
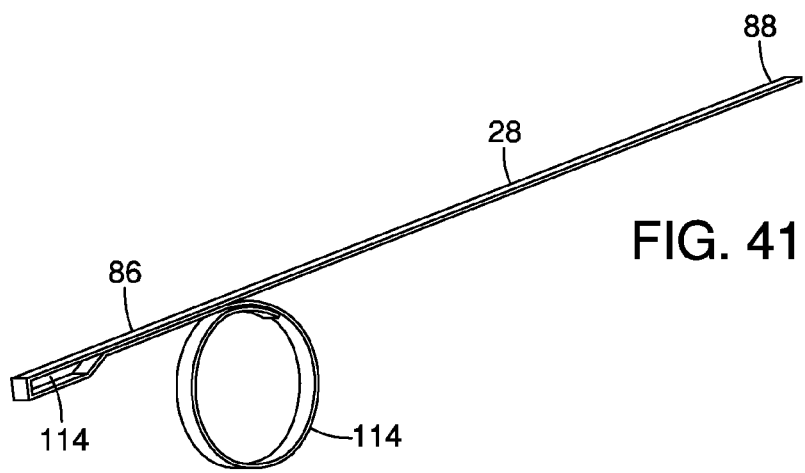
FIG. 41 illustrates an embodiment of the material portion having a loop.

FIGS. 39-40 illustrate embodiments of the material portion 28 formed from a flattened material that includes one or more undulations 116 in the proximal portion 86 of the material portion 28. The material may be any of the materials described above. The width and the thickness of the material portion 28 may be varied from the proximal portion 86 to the distal portion 88. FIG. 41 illustrates an embodiment of the material portion 28 including a plurality of loops 114 at the proximal portion 86. The width and the thickness of the material portion 298 may narrow toward the distal portion 88 of the material portion 28 in some embodiments. FIGS. 42A-42C illustrate an embodiment of the material portion 28 having a plurality of coils 104 extending generally perpendicular to the bottom of the "u" of the distal portion 88. The coils 104 are shown flexing in response to a pressure exerted on the material portion in FIGS. 42B and 42C.

Figure 43A:
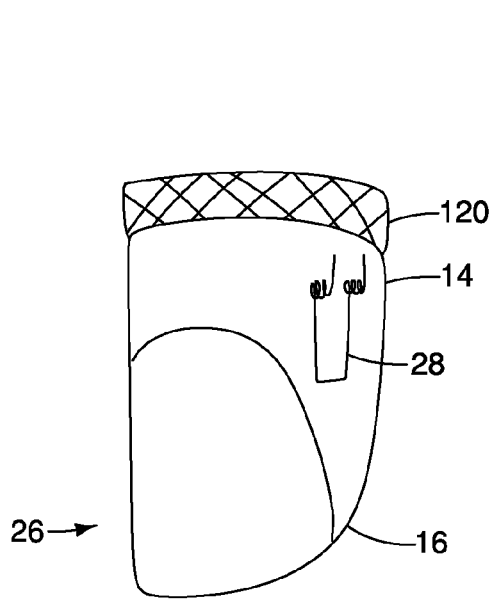
FIGS. 43A and 43B illustrate embodiments of a retrofit valve.
Figure 43B:
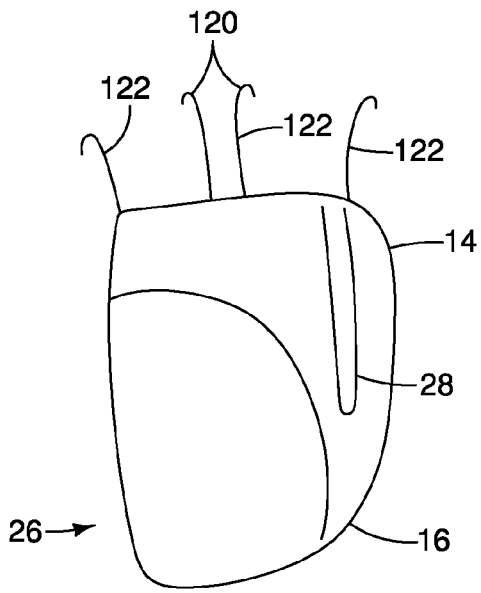

In some embodiments, the valve 26 may be retrofit into an existing body 12 of a prosthesis 10 that has already been positioned within a patient's lumen. The retrofit valves may have any of the features described and may also include an attachment member to attach the valve to the existing body. As shown in FIGS. 43A and 43B, the valve 26 may include an attachment member 120 that is configured to position the valve 26 within the body 12 and hold the valve 26 within the body. The attachment member 120 may be connected to the proximal portion 14 of the valve 26 as shown, although other attachment positions for the attachment member 120 are also possible. By way of non-limiting example, the attachment member 120 may be provided as an expandable mesh that expands to conform to the shape of the lumen of the body 12 into which the valve 26 is positioned as shown in FIG. 43 A. In other embodiments, the attachment member 120 may be provided as a plurality of connectors 122 that are configured to connect to the stent to hold the vale 26 in position. Other methods and attachment members may also be used to secure the retrofit valve 26 to the body 12.

Figure 44:
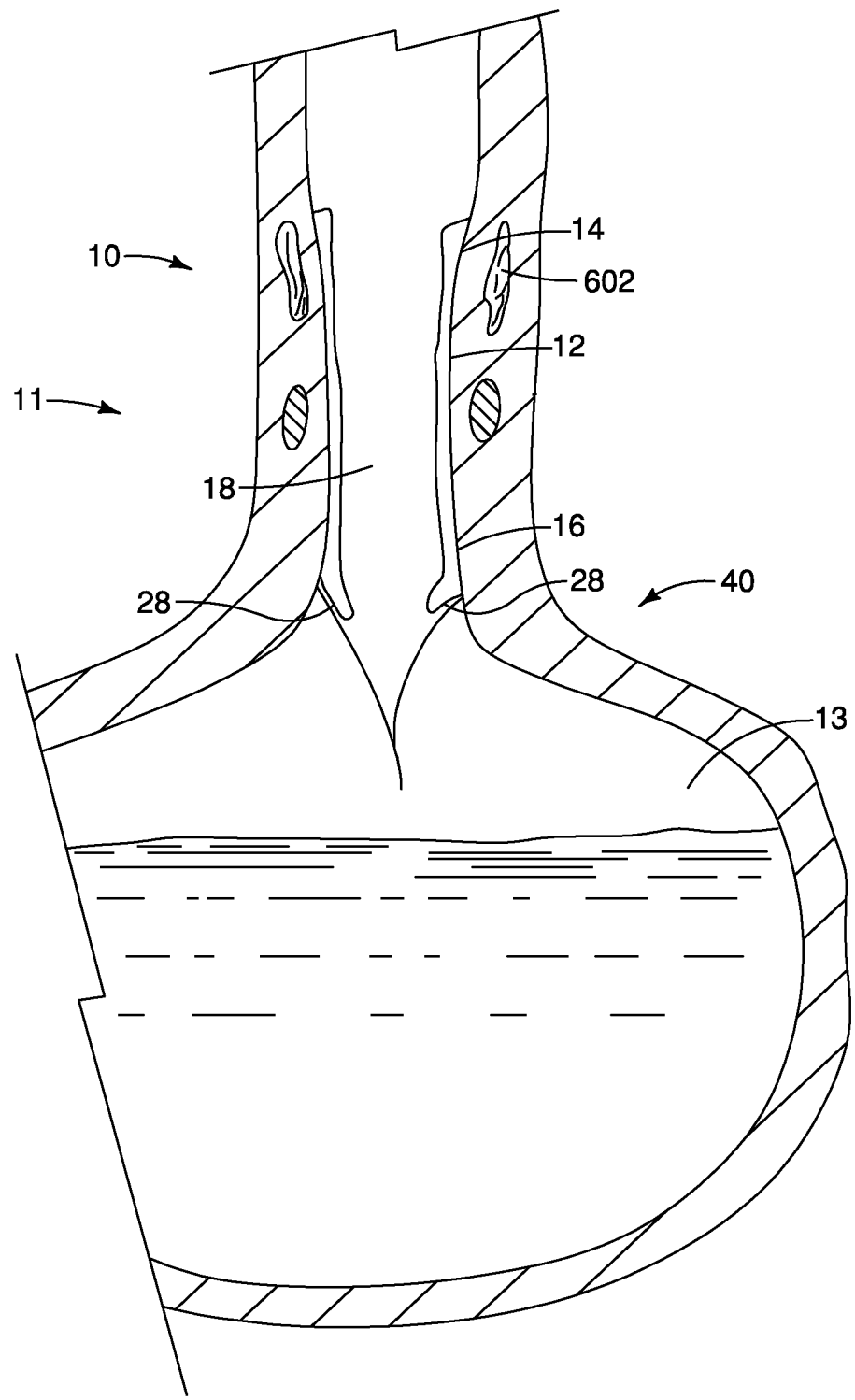
FIG. 44 is an illustration of a prosthesis positioned within the lower esophageal sphincter.

As shown in FIG. 44, the prosthesis 10 may be positioned in the lower esophageal sphincter (LES) 11. The prosthesis 10 may be delivered to the LES using a delivery catheter such as the EVOLUTION delivery system (Cook Medical Incorporated, Bloomington, Ind., not shown) and positioned in the LES. Other types of delivery systems may also be used. The proximal portion 14 of the body 12 may be positioned proximal to the esophageal sphincter 11. The distal portion 16 of the body 12 may be positioned so that the distal portion 16 and/or the valve 26 extend into the stomach 13. As shown, the body 12 extends across a growth 602 that may be occluding the esophagus. The valve 26 normally remains closed in the absence of the second and third pressures 44, 50 described above.

The materials used to manufacture the components of the prosthetic devices described herein may be any materials known to one skilled in the art that are suitable for use in patients. By way of non-limiting example, the body may be formed from metals or polymers. Suitable exemplary metals include stainless steel and nitinol and the body may be woven or provided in a zig-zag configuration. Valves of the prosthetic devices of the embodiments may be made from any suitable biocompatible material that is liquid impermeable and that does not degrade in the presence of fluids or gastric material that comes in contact therewith. By way of non-limiting example, the valve may be made from a medical grade polyurethane material, silicone, nylon, polyamides such as other urethanes, or other biocompatible materials that are flexible and acid resistant. An exemplary material for the valve is a medical grade polyurethane material grade EG-80A material commercially known as TECOTHANE®; polyurethane material (Thermedics, Incorporated, Woburn, Mass.) or medical grade silicon. The material portion may be formed from a metal or a polymer. By way of non-limiting example, the material portion may be formed from nitinol. In some embodiments, the material portion is made from a different material than the valve. Examples of suitable materials include, polymers, such as polytetrafluoroethylene (PTFE), polyurethane, shape memory poly-urethane, and poly-silicone. UHMW Poly-ethylene; elastomeric Poly-ethylene; LD Poly-ethylene; HD Poly-ethylene; Poly-propylene; Elastomeric PTFE; polyethylene terephthalate (PET); polyethyleneoxide (PEO), and block copolymers containing polystyrene and poly(1,4-butadiene), and an ABA triblock copolymer made from poly(2-methyl-2-oxazoline) and poly-tetrahydrofuran, amorphous or organic-inorganic hybrid polymers comprising polynorbornene units and shape memory polymers. In some embodiments, portions of the prosthesis may be radiopaque or may include one or more radiopaque markers.

The valve of the embodiments described above may be formed as follows. For example, when nitinol is used to from the material portion, the material portion may be formed on a metal mandril in to the desired shape. The shape is then heat set so the nitinol wants to remain in the set shape. To make the valve, and optionally the coated body, the valve mandril is dipped into a solution, by way of non-limiting example a silicone or a poly-urethane polymer dispersion. In some embodiments, the valve mandril may be made of PTF, anodized aluminum; glass; DACRON (polyethylene terephthalate), mild steel and stainless steel. The polymer dispersion solution provides and inner surface for the valve that is then cured. The heat set nitinol structure is transferred to the valve mandril on top of the cured polymer dispersion inner layer. The polymer dispersion layer and the heat set nitinol structure are then dipped again into the polymer dispersion. The shape of the metal mandril and the valve mandril are different so that when the valve is produced, the nitinol tries to force the valve into a specific configuration. The axis of the body 12 of a woven stent may be different than the axis of a woven material portion. In some embodiments, the material portion may be suspended into the valve. In some embodiments, the valve may be formed by an electrospinning process, using heat shrink tubing, blow molding process, extruding, molding, weaving and heat forming a polymer material over the a mold with the required shape. Any suitable method known to one skilled in the art may be used to form the valve.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A prosthesis for controlling flow through a bodily lumen, the prosthesis comprising:
   a body having a proximal portion, a distal portion, a distal end and a lumen extending therethrough; and
   a valve operably connected to the body, the valve having a proximal portion, a distal end portion and a lumen extending through the valve, the valve lumen connected to the body lumen; the valve having a closed configuration in the absence of an antegrade pressure and a retrograde pressure, and an open configuration wherein the distal end portion of the valve extends proximally in response to the retrograde pressure, the retrograde pressure being greater than the antegrade pressure, the distal end portion of the valve is positioned distal to the distal end of the body in the closed configuration; the valve comprising a material portion operably connected to the valve on a surface of the valve or embedded in the valve, the material portion comprising:
   a distal end, a body portion and a coil, the body portion of the material portion extends proximally from the distal end of the material portion and the coil is formed in the body portion of the material portion and positioned proximal to the distal end of the material portion in the closed configuration of the valve, the material portion providing increased stiffness to the valve relative to the valve alone, the material portion having a first position in the closed configuration and a second position in the open configuration, a distal portion of the material portion bends inward towards the valve lumen to the second position to facilitate proximal extension of the distal end portion of the valve to move the valve to the open configuration in response to the retrograde pressure, wherein the material portion facilitates self-reversion of the valve to the closed configuration wherein the distal end portion of the valve extends distally, the valve allowing flow through the valve in response to retrograde pressure and antegrade pressure when the prosthesis is implanted.

2. The prosthesis of claim 1, wherein the material portion comprises at least one material that is different from a valve material.

3. The prosthesis of claim 1, wherein the material portion comprises nitinol.

4. The prosthesis of claim 3, wherein the nitinol is heat set.

5. The prosthesis of claim 1, wherein the material portion is connected to the distal portion of the body.

6. The prosthesis of claim 1, wherein the material portion at least partially overlaps the body.

7. The prosthesis of claim 2, wherein the material portion comprises one arm.

8. The prosthesis of claim 2, wherein the material portion comprises one u-shaped arm.

9. The prosthesis of claim 1, wherein the material portion comprises a proximal portion and the distal portion of the material portion is more flexible than the proximal portion of the material portion.

10. The prosthesis of claim 9, wherein the distal portion of the material portion is electropolished, ground or chemically etched to provide flexibility.

11. The prosthesis of claim 1, wherein the distal end of the material portion is movable proximally in response to the retrograde pressure to facilitate opening the valve in response to the retrograde pressure.

12. The prosthesis of claim 1, wherein the distal end of the material portion is movable to facilitate a return of the valve to the closed configuration after the retrograde pressure is removed.

* * * * *